(12) United States Patent
Reinboth et al.

(10) Patent No.: US 8,215,304 B2
(45) Date of Patent: Jul. 10, 2012

(54) DEVICE FOR SEPARATING CONDENSATE FROM A COAXIAL BREATHING GAS LINE

(75) Inventors: Thomas Reinboth, Großhansdorf (DE); André Huschke, Hamburg (DE); Axinja Schönbeck, Klingberg (DE)

(73) Assignee: Dräger Medical GmbH, Lübeck (DE)

( * ) Notice: Subject to any disclaimer, the term of this patent is extended or adjusted under 35 U.S.C. 154(b) by 467 days.

(21) Appl. No.: 12/571,644

(22) Filed: Oct. 1, 2009

(65) Prior Publication Data
US 2010/0122702 A1 May 20, 2010

(30) Foreign Application Priority Data

Nov. 14, 2008 (DE) .................... 10 2008 057 345

(51) Int. Cl.
*A61M 16/00* (2006.01)
*A61M 16/20* (2006.01)
(52) U.S. Cl. ......... 128/205.12; 128/205.27; 128/204.16; 128/205.24; 128/911; 128/912
(58) Field of Classification Search ............ 128/205.12, 128/205.27, 204.16, 205.24, 911, 912
See application file for complete search history.

(56) References Cited

U.S. PATENT DOCUMENTS

| 4,457,305 | A | | 7/1984 | Shanks et al. |
| 4,867,153 | A | * | 9/1989 | Lorenzen et al. ......... 128/205.12 |
| 5,168,868 | A | * | 12/1992 | Hicks ....................... 128/205.12 |
| 5,433,194 | A | * | 7/1995 | Fry ........................... 128/205.12 |
| 7,383,852 | B2 | * | 6/2008 | Pittaway et al. .............. 137/171 |
| 2002/0017302 | A1 | * | 2/2002 | Fukunaga et al. ........ 128/207.14 |

FOREIGN PATENT DOCUMENTS

| DE | 3742888 A1 | 7/1989 |
| GB | 1456570 A | 11/1976 |
| GB | 2272745 A | 5/1994 |
| GB | 2384844 A | 8/2003 |
| WO | WO 01/62313 A2 | 8/2001 |

* cited by examiner

*Primary Examiner* — Clinton T Ostrup
(74) *Attorney, Agent, or Firm* — McGlew and Tuttle, P.C.

(57) ABSTRACT

A condensate separator is provided for a coaxial tube system, which has an inner gas duct (3) and an outer gas duct (4). A first liquid duct (10) is arranged between the inner gas duct and a first collection volume (8) and a second liquid duct (11) is located between the outer gas duct (4) and a second collection volume (9). The collection volumes (8, 9) are located with a partition (7) in between in a liquid collecting container (6).

4 Claims, 3 Drawing Sheets

DEVICE FOR SEPARATING CONDENSATE FROM A COAXIAL BREATHING GAS LINE

CROSS REFERENCE TO RELATED APPLICATIONS

This application claims the benefit of priority under 35 U.S.C. §119 of German Patent Application 10 2008 057 345.0 filed Nov. 14, 2008, the entire contents of which are incorporated herein by reference.

FIELD OF THE INVENTION

The present invention pertains to a device for separating condensate from a coaxial breathing gas line.

BACKGROUND OF THE INVENTION

A device of this type is known from U.S. Pat. No. 4,457,305. The device, hereinafter called "water trap," comprises an inlet duct and an outlet duct for breathing gas, which are arranged at an angle to one another. A liquid duct, which can be closed by a valve, is located at the deepest point, in order to remove the condensate from the breathing gas duct. The liquid duct opens into a liquid container, which is pushed over a connecting flange. A pin, which points in the direction of the valve and has such a length that a valve body lifts the valve from its valve seat by the pin when the liquid collecting container is connected to the connecting flange, is located at the bottom surface of the liquid collecting container. With the valve opened, the condensate can flow off from the breathing gas duct into the liquid collecting container. If, by contrast, the liquid collecting container is removed from the connecting flange, the valve body lies on the valve seat and the liquid duct is closed. The valve arranged in the liquid duct is also used to close the breathing gas duct against the environment in order to prevent breathing gas from escaping into the environment when the liquid collecting container is removed.

So-called tube-in-tube systems, which have an inner gas duct and an outer gas duct arranged concentrically thereto in order to send inspiration gas to the patient and to take up expired gas, are also used to respirate patients. Since humidified breathing gas is usually used during respiration, condensate, which must be drawn off, may occur in both gas ducts. Even though it would be possible to provide a separate water trap for each gas duct, this would make handling difficult, because two liquid collecting containers must always be checked and optionally removed during the operation. The use of two separate water traps is possible in the coaxial tube system by technically complicated measures only. Thus, the outer gas duct must be sealed during the removal of the condensate from the inner gas duct. The flow characteristic in the outer gas duct may change in this case and lead to an increase in flow resistance there.

SUMMARY OF THE INVENTION

The basic object of the present invention is to provide a condensate separator for a coaxial tube system, which is easy to handle and with which mixing of the gas flows being carried in the gas ducts is prevented from occurring.

According to the invention, a device is provided for separating condensate from breathing gas. The device includes a breathing gas line comprising an inner gas duct and an outer gas duct arranged concentrically thereto. A liquid collecting container is provided with a first collection volume and with a second collection volume and with a partition between the first collection volume and the second collection volume. A connecting flange, at the breathing gas line, is provided for receiving the liquid collecting container. The connecting flange has a first liquid duct between the inner gas duct and the first collection volume and a second liquid duct between the outer gas duct and the second collection volume. A first shut-off valve is provided in the first liquid duct and a second shut-off valve is provided in the second liquid duct. A first valve lifter and a second valve lifter are provided at the liquid collecting container, by which the shut-off valves are switched into the closed position when the liquid collecting container is removed and are switched into the open position when the liquid collecting container is pushed over the connecting flange (i.e., when connected).

The shut-off valves may comprise valve bodies actuated by the valve lifters. The valve bodies may be lifted off from valve seats.

The breathing gas tube may comprise an inner gas duct and an outer gas duct in a coaxial arrangement.

According to a further aspect of the invention, a process is provided for separating condensate from a breathing gas tube. The tube has an inner gas duct and an outer gas duct in a coaxial arrangement. The process includes providing and connecting a device with a liquid collecting container provided with a first collection volume and with a second collection volume and with a partition between the first collection volume and the second collection volume. A connecting flange, at the breathing gas line, is provided for receiving the liquid collecting container. The connecting flange has a first liquid duct between the inner gas duct and the first collection volume and a second liquid duct between the outer gas duct and the second collection volume. A first shut-off valve is provided in the first liquid duct and a second shut-off valve is provided in the second liquid duct. A first valve lifter and a second valve lifter are provided at the liquid collecting container, by which the shut-off valves are switched into the closed position when the liquid collecting container is removed and are switched into the open position when the liquid collecting container is connected.

The advantage of the device according to the present invention is that the inner gas duct and the outer gas duct of the coaxial tube system have separate liquid ducts for draining off the condensate and the liquid collecting container is divided into two separate collection volumes by means of a partition. A first liquid duct for drawing off condensate from the inner gas duct leads into a first collection volume and a second liquid duct is connected to the outer gas duct and to a second collection volume. Mixing of the breathing gas of the inner gas duct with that in the outer gas duct is prevented by the partition between the first collection volume and the second collection volume.

When the liquid collecting container is removed, shut-off valves are closed in both liquid ducts, so that no breathing gas can escape into the environment and the condensate collected in the collection volumes can be disposed of simultaneously for the entire tube system. The liquid ducts between the gas ducts and the collection volumes require only a small cross-sectional area within the gas ducts, so that the breathing gas flow is hardly hindered and only a negligible increase will occur in the flow resistance.

An exemplary embodiment of the present invention is shown in the drawings and will be explained in more detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
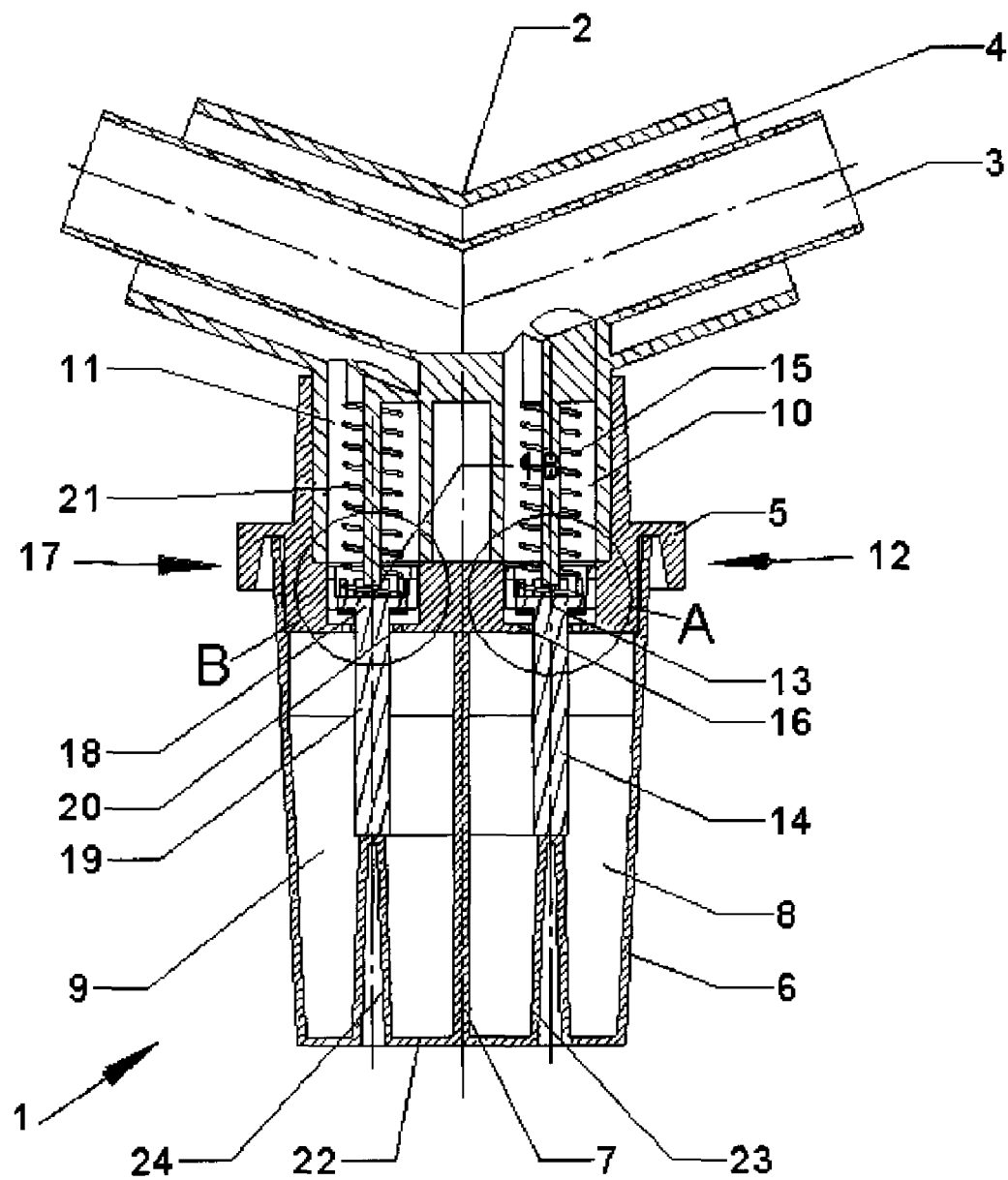
FIG. 1 is a longitudinal section through a water trap.

Referring to the drawings in particular, FIG. 1 schematically illustrates the design of a water trap 1 according to the present invention in the longitudinal section. A breathing gas line 2, shown as a section only, has an inner gas duct 3 and an outer gas duct 4 arranged concentrically thereto with mutually opposite directions of flow for the breathing gas. The breathing gas line 2 is lowered downward at an obtuse angle, and a connecting flange 5 for a liquid collecting container 6 is located at the deepest point.

The liquid collecting container 6 has a partition 7, which separates a first collection volume 8 from a second collection volume 9. A first liquid duct 10 leads from the inner gas duct 3 into the first collection volume 8 and a second liquid duct 11 connects the outer gas duct 4 with the second collection volume 9. A first shut-off valve 12 arranged within the first liquid duct 10 comprises a first valve body 13 with a first pin-like extension 14, which is pressed by means of a first valve spring 15 against a first valve seat 16. A second shut-off valve 17 arranged in the second liquid duct 11 correspondingly comprises a second valve body 18 with a second pin-like extension 19, a second valve seat 20 and a second valve spring 21.

A first valve lifter 23 extends in the direction of the first pin-like extension 14 from the bottom of the liquid collecting container 6 at right angles to the bottom surface 22 within the first collection volume 8 and a second valve lifter 24 extends in the direction of the second pin-like extension 19 within the second collection volume 9.

When the liquid collecting container 6 is located at the connecting flange 5, the valve lifters 23, 24 are in contact with the pin-like extensions 14, 19, as a result of which the valve bodies 13, 18 are lifted off from the corresponding valve seats 16, 20 against the force of the valve springs 15, 21 and condensate can flow off from the inner gas duct 3 into the first collection volume 8 and from the outer gas duct 4 into the second collection volume 9. With the liquid collecting containers 6 removed, the valve bodies 13, 18 lie on the corresponding valve seats 16, 20 and the connections are interrupted.

Figure 2:
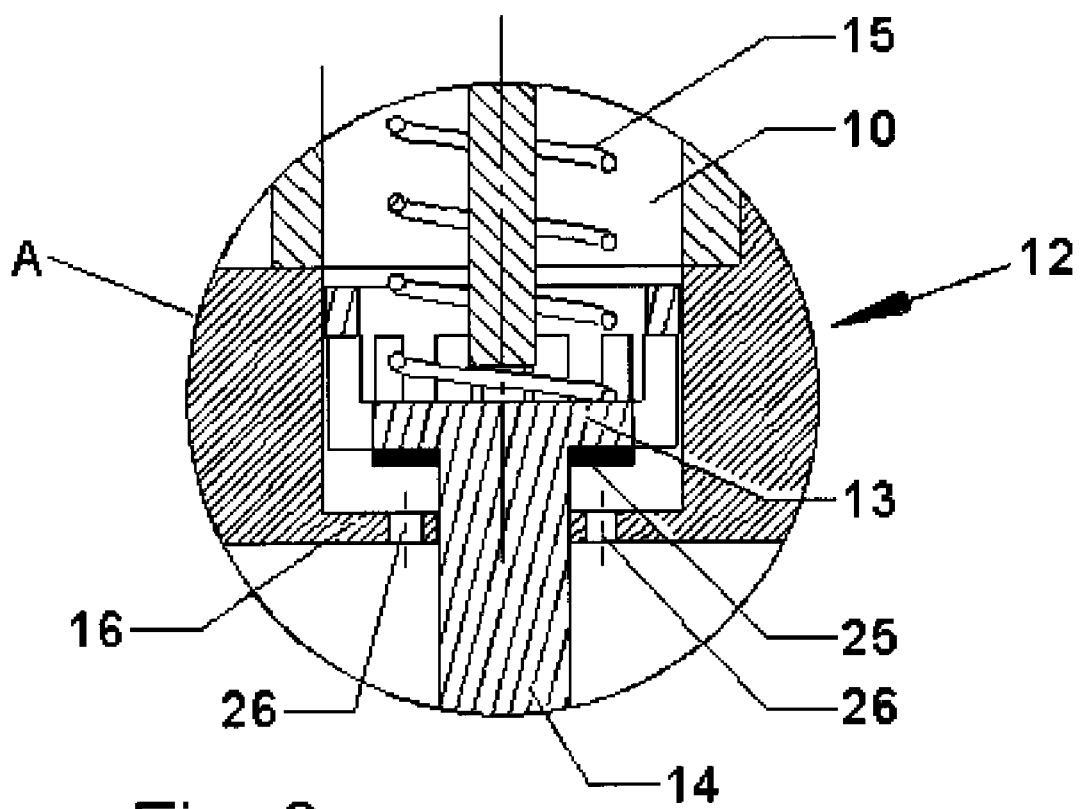
FIG. 2 is a view of detail A according to FIG. 1.
Figure 3:
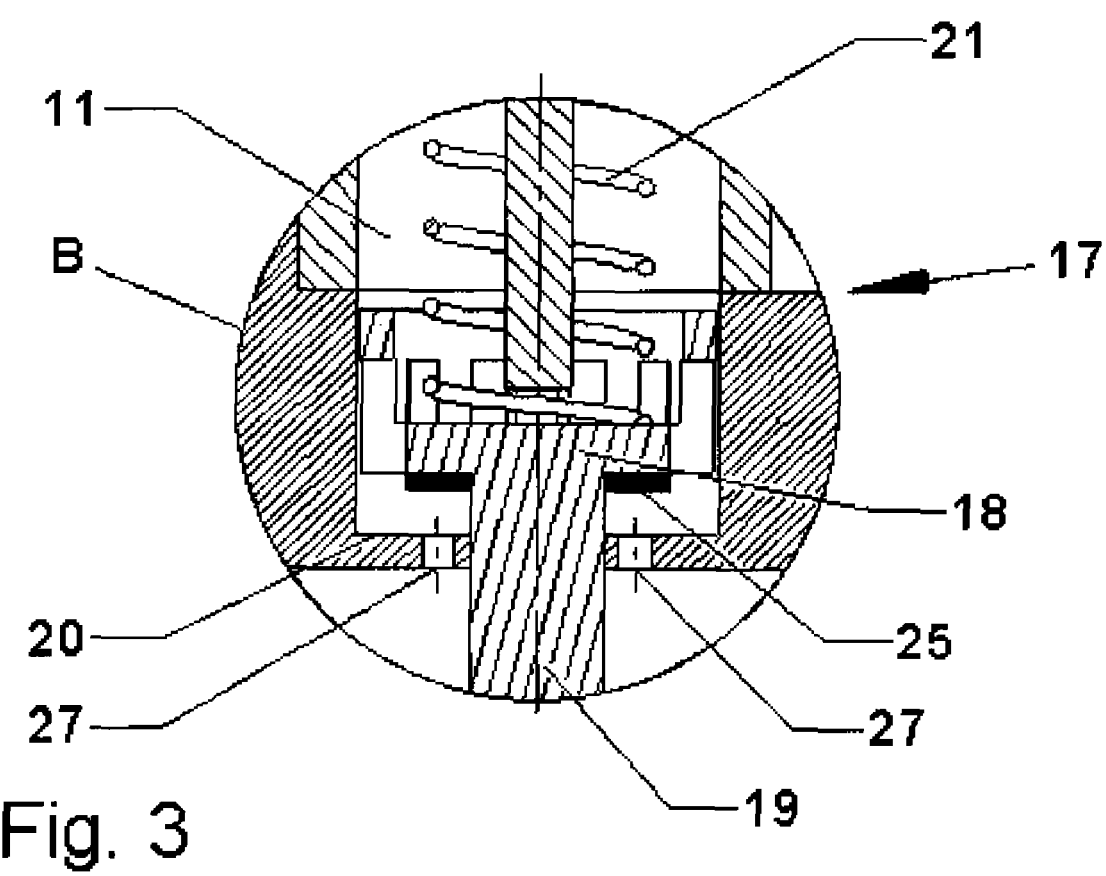
FIG. 3 is a view of detail B according to FIG. 1.

FIGS. 2 and 3 show the details A and B corresponding to FIG. 1. Identical components are designated by the same reference numbers as in FIG. 1. Sealing washers 25, with which through holes 26, 27 in the area of the liquid ducts 10, 11 are closed in order to prevent condensate from flowing off when the liquid collecting container 6 has been removed, are arranged on the underside of the valve bodies 26, 27. First through holes 26 are located in the area of the first valve seat 16 and second through holes 27 in the area of the second valve seat 20 to drain off condensate.

While a specific embodiment of the invention has been described in detail to illustrate the application of the principles of the invention, it will be understood that the invention may be embodied otherwise without departing from such principles.

What is claimed is:

1. A device for separating condensate from breathing gas, the device comprising:
a breathing gas line comprising an inner gas duct and an outer gas duct arranged concentrically thereto;
a liquid collecting container with a first collection volume and with a second collection volume and with a partition between the first collection volume and the second collection volume;
a connecting flange provided at the breathing gas line for receiving the liquid collecting container, wherein the connecting flange has a first liquid duct between the inner gas duct and the first collection volume and a second liquid duct between the outer gas duct and the second collection volume;
a first shut-off valve in the first liquid duct;
a second shut-off valve in the second liquid duct;
a first valve lifter at the liquid collecting container; and
a second valve lifter at the liquid collecting container, by which the shut-off valves are switched into the closed position when the liquid collecting container is removed and into the open position when the liquid collecting container is connected.

2. A device in accordance with claim 1, wherein the shut-off valves have valve bodies, which are actuated by the valve lifters and can be lifted off from valve seats.

3. A process for separating condensate from a breathing gas tube, the process comprising:
providing a breathing gas line comprising an inner gas duct and an outer gas duct arranged concentrically thereto;
providing a liquid collecting container with a first collection volume and with a second collection volume and with a partition between the first collection volume and the second collection volume;
connecting a connecting flange to the breathing gas line wherein the connecting flange has a first liquid duct between the inner gas duct and the first collection volume and a second liquid duct between the outer gas duct and the second collection volume;
providing a first shut-off valve in the first liquid duct;
providing a second shut-off valve in the second liquid duct;
providing a first valve lifter at the liquid collecting container;
providing a second valve lifter at the liquid collecting container; and
switching the shut-off valves into a closed position using the first valve lifter and the second valve lifter when the liquid collecting container is removed from a connected position with the connecting flange and switching the shut-off valves into an open position when the liquid collecting container is connected in the connected position with the connecting flange.

4. A condensate separating device comprising:
a breathing gas line comprising an inner gas duct and an outer gas duct;
a connecting flange with a first liquid duct leading from the inner gas duct and with a second liquid duct leading from the outer gas duct, the connecting flange having a connecting portion;
a liquid collecting container with a first collection volume and with a second collection volume and with a partition between the first collection volume and the second collection volume, the liquid collecting container including a portion for connection with the connecting portion of the connecting flange with the first liquid duct in fluid communication with the first collection volume and the second liquid duct in fluid communication with the second collection volume;

a first shut-off valve in the first liquid duct;

a second shut-off valve in the second liquid duct;

a first valve lifter responsive to the position of the liquid collecting container and acting on the first shut-off valve for switching the first shut-off valve between a closed position when the collecting container portion is removed from the connecting portion of the connecting flange and an open position when the collecting container portion is connected to the connecting portion of the connecting flange; and a second valve lifter responsive to the position of the liquid collecting container and acting on the second shut-off valve for switching the second shut-off valve between a closed position when the collecting container portion is removed from the connecting portion of the connecting flange and an open position when the collecting container portion is connected to the connecting portion of the connecting flange.

* * * * *